United States Patent [19]

Hiltebrandt

[11] 4,345,589
[45] Aug. 24, 1982

[54] ENDOSCOPIC INSTRUMENTATION APPARATUS

[75] Inventor: Siegfried Hiltebrandt, Knittlingen, Fed. Rep. of Germany

[73] Assignee: Richard Wolf GmbH, Knittlingen, Fed. Rep. of Germany

[21] Appl. No.: 148,755

[22] Filed: May 12, 1980

[30] Foreign Application Priority Data

May 15, 1979 [DE] Fed. Rep. of Germany ... 7913986[U]

[51] Int. Cl.³ .............................................. A61B 1/00
[52] U.S. Cl. ........................................ 128/4; 128/348
[58] Field of Search ...................... 128/4, 6, 7, 8, 347, 128/348, 303.15, 329 R

[56] References Cited

U.S. PATENT DOCUMENTS 1,527,291 2/1925 Zorraquin ........................ 128/347 X

FOREIGN PATENT DOCUMENTS 103884 3/1942 Sweden .................................. 128/8

Primary Examiner—Michael H. Thaler

Attorney, Agent, or Firm—Kinzer, Plyer, Dorn & McEachran

[57] ABSTRACT

This invention relates to endoscopic instrumentation apparatus and comprises a puncture cannula and a related hollow mandrel and optical system connectible to a coupling element of the puncture cannula; a hollow cylindrical intermediate element is also connectible to said coupling element of the puncture cannula and there are valved connectors fitted to the puncture cannula and the hollow mandrel, said valved connectors also being connectible to an automatic gas supply. The coupling element of the cannula is constituted by a hollow shaft which is installed for displacement against a spring towards a proximal end of the cannula; the hollow mandrel extends distally beyond an oblique face of the cannula and the intermediate element and the cannula are traversed by a connectible optical system which projects distally at least beyond the oblique face of the puncture cannula.

The apparatus can be used for performing laparoscopy and culdoscopy operations or examinations.

1 Claim, 8 Drawing Figures

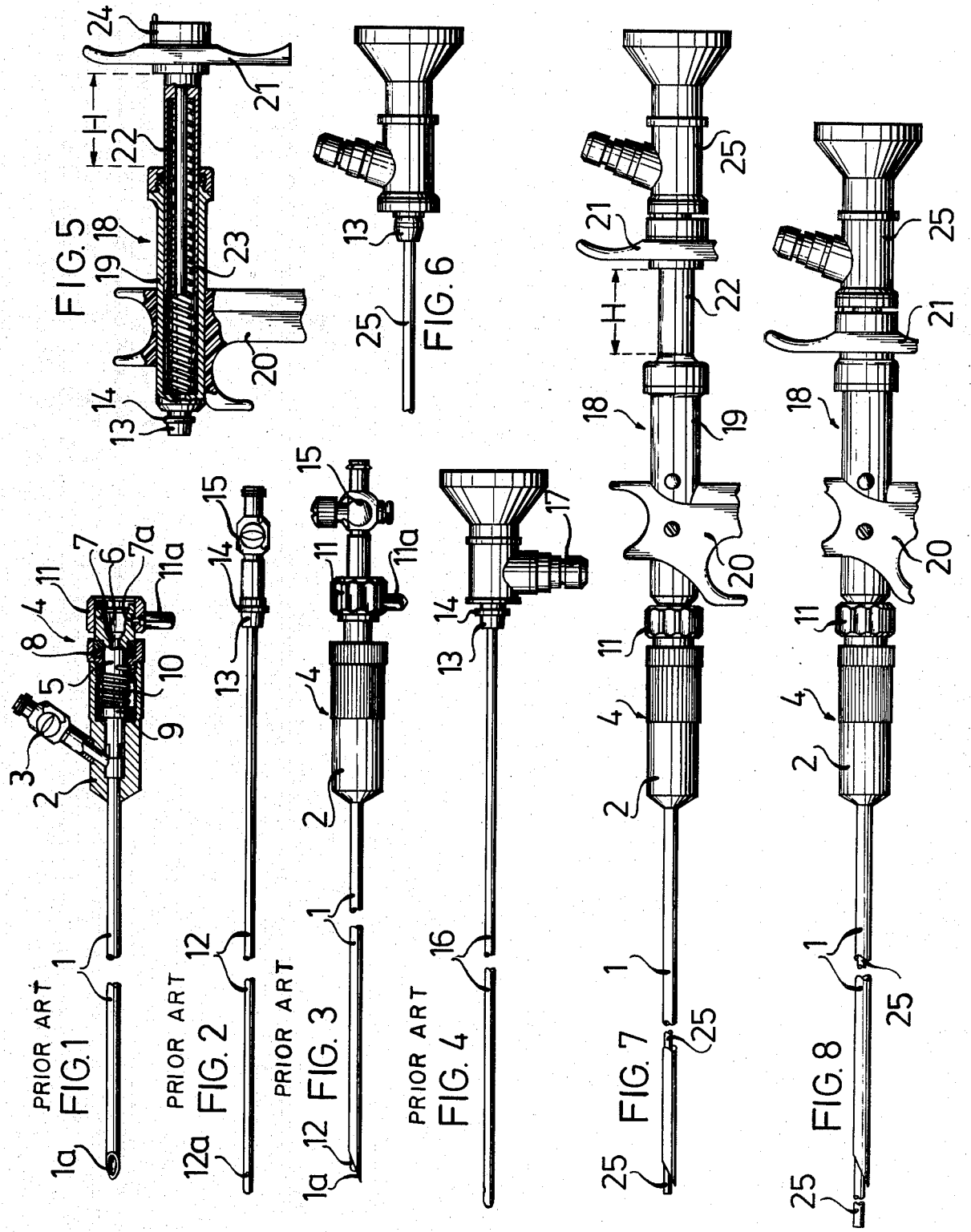

ENDOSCOPIC INSTRUMENTATION APPARATUS

BACKGROUND OF THE INVENTION

The present invention relates to endoscopic instrumentation apparatus for performing laparoscopy and culdoscopy operations.

It has already been proposed to utilise a puncture cannula (Veres cannula) having an oblique face at the far end and a connector at the near end for connection to an automatic gas supply, for performing laparoscopy operations. After plunging the puncture cannular into the abdominal cavity, the application of a pneumoperitoneum is performed by connection of the puncture cannula to an automatic gas supply, without any optical monitoring of the position of the cannula and of its oblique end face. This establishes the risk that organs may be punctured, and the greatest danger consists in that large quantities of gas may be blown into a punctured organ, e.g. the intestine, a large blood vessel or the like.

It is an object of the invention to provide endoscopic instrumentation apparatus from parts fitting to each other, in such manner that laparoscopic as well as culdoscopic examinations may be performed therewith and that immediately after penetration, the correct penetration into the unobstructed ventral space can be performed under optical observation before large volumes of gas are blown into the abdominal cavity.

SUMMARY OF THE INVENTION

Accordingly, the invention consists in endoscopic instrumentation apparatus for performing laparoscopy and culdoscopy, comprising:

(a) a puncture cannula having a distal oblique face and a proximal cylindrical casing in which a coupling element constituted by a hollow shaft is installed for displacement against a spring towards the proximal end, (b) a hollow mandrel and related optical system connectible to said coupling element of said puncture cannula and extending distally beyond said oblique face of said puncture cannula, (c) a hollow cylindrical intermediate element which is reducible in length against a spring and is connectible to said coupling element of said puncture cannula, said intermediate element and said puncture cannula being traversed by a second connectible optical system which projects distally at least beyond said oblique face of said puncture cannula, and (d) valved connectors fitted to said puncture cannula and said hollow mandrel with said valved connectors being also connectible to an automatic gas supply.

This instrumentation enables laparoscopic examinations to be performed in a simplified manner, and under application of the same puncture cannula with the mandrel and under application of the intermediate element as well as of a longer complementary optical system, to perform culdoscopic examinations. Above all, the mandrel may be replaced rapidly and easily by the optical system after transpiercing the abdominal walls and insufflation of small gas volumes by means of the mandrel, thereby immediately providing an optical check on the correct position of the puncture cannula and complementarily rendering it possible to verify whether any organs have been punctured. It is only after this optical check that the pneumoperitoneum is brought to its full value in the bodily cavity via the puncture cannula.

In the case of concrescences, e.g. in the case of patients previously operated on, this verification is of special importance to avoid puncturing the concrescences and to avert the occurrence of sizable haermorrhages. In the case of such patients previously operated on, it may be necessary to introduce the puncture cannula via the vaginal vault, use then being made of the intermediate element with the longer optical system, to come closer to the object.

BRIEF DESCRIPTION OF THE DRAWINGS

In order that the invention may be more clearly understood, reference will now be made to the accompanying drawings, which show an embodiment thereof by way of example, and in which:

FIG. 1 shows a puncture cannula comprising a known proximal mechanism in sideview and in axial cross-section at the proximal end, FIG. 2 shows a mandrel insert in sideview, FIG. 3 shows a sideview of the cannula of FIG. 1 rotated through 90°, with the mandrel according to FIG. 2 being inserted but already thrust towards the proximal end, FIG. 4 shows the optical system which may be substituted for the mandrel according to FIG. 2, in sideview, FIG. 5 shows an intermediate element for connection to the puncture cannula according to FIG. 1, in axial cross-section, FIG. 6 shows the longer optical system required in case of making use of the intermediate element according to FIG. 5, in partial sideview, FIG. 7 shows the assembled instrumentation comprising the puncture cannula according to FIG. 1, the intermediate element according to FIG. 5, and the optical system according to FIG. 6, in sideview, and FIG. 8 shows the apparatus according to FIG. 7, but with the optical system extruded at the far end.

DETAILED DESCRIPTION OF PREFERRED EMBODIMENT

Referring now to the drawings, in accordance with the invention, use is made of a puncture cannula according to FIG. 1, which comprises a shaft 1 having an oblique distal face 1a and a cylindrical causing 2 enlarged at the proximal end and having external grooving and with a valved connector 3 for connection to an automatic gas supply.

Within the casing 2 is situated a coupling 4 comprising a guided hollow shaft 5 with a hollow proximal coupling cone 6 of a cylindrical extension 7. The hollow shaft 5 is externally sealed against the casing 2 by means of a sealing ring 8 and is thrust via a flange 9 against an internal casing step at the far end by means of a lightly pre-loaded spring 10.

At its periphery, the cylindrical extension 7 is provided with a bayonet joint recess 7a in which engages the inner extremity of a bar 11a which traverses the side of a screw cap 11 and serves the purpose of turning the cap.

A hollow cylindrical mandrel 12 having a distal egress aperture 12a and closed off in rounded form at the distal extremity may be incorporated in the puncture cannula 1 according to FIG. 1, and at the proximal end, the mandrel is provided with a coupling cone 13 fitting into the hollow cone 6, also with a collar 14 and a tap 15 for connection to an automatic gas supply. This mandrel 12 is inserted into the puncture cannula according to FIG. 1 and the cones 6 and 13 are kept in coupled engagement by the screw cap 11. At the distal end the mandrel also projects out of the shaft 1 of the puncture cannula and beyond the latter, so that the acute oblique end face cannot normally cause injuries.

For transpiercing the abdominal walls, the puncture cannula 1 is first placed with the distal extremity of the mandrel on the abdominal wall, and an axial thrust is then applied on the proximal end due to the presence of the yielding spring 10, so that the oblique face 1a may pierce the abdominal wall. Immediately after careful piercing of the abdominal wall, the mandrel 1 is propelled forward again by the spring 10 and projects out of the oblique face 1a at the distal end, so that the oblique face then cannot cause any injury to internal parts.

The tap 15 of the mandrel is then opened, so that a supply of gas from an automatic gas dispenser is released into the body cavity. The tap 15 is closed again after a provisional pneumoperitoneum is obtained.

After freeing the proximal coupling, the mandrel 12 is then drawn out of the puncture cannula 1 and is replaced by insertion of an optical system according to FIG. 4 into the cannula 1, which is again coupled via a cone 13 and collar 14 to the hollow cone 6 of the cannula and secured in position by the screw cap 11. The optical system 16 then equally projects beyond the oblique face 1a of the puncture cannula 1 at the distal extremity. The optical tube 16 is traversed in known manner by optical fibres terminating at the near end in a connector 17 where they are connected to a light ducting cable leading to a projector, so that the examination may be made under illumination of the object.

The tap 3 is opened after insertion of the optical system according to FIG. 4 through the puncture cannula, so that gas may then flow from an automatic gas supply into the body cavity until the final gas pressure has been reached in the cavity. The supply of gas into the cavity via the tap 3 of the puncture cannula is thus a complement to the supply of gas via the tap 15 of the mandrel to build up the finally required gas pressure.

The invention also enables the puncture cannula according to FIG. 1, and a mandrel according to FIG. 2, to be employed for culdoscopic examinations. In this case, after piercing the abdominal wall by means of the puncture cannula 1, the mandrel 12 is withdrawn from the cannula 1 and an intermediate element 18 according to FIG. 5 is coupled to the puncture cannula.

As shown in FIG. 5, the intermediate element 18 comprises a hollow cylinder 19 closed off by a coupling cone 13, 14 and has an external handle 20. A hollow cylinder 22 closed off at the proximal end by a counter-handle 21 is located in the cylinder 19, and is supported in the cylinder 19 by a spring 23. The proximal extremity 24 of the internal cylinder 22 is also provided, like the puncture cannula 1, with a hollow cone like cone 6 for coupling engagement of a cone 13.

The intermediate element 18 according to FIG. 5 is coupled to the puncture cannula 1 by means of the cones 6 and 13 and the screw cap 11 in a bayonet joint, and an optical system 25 according to FIG. 6 is then passed through the intermediate element 18 and the puncture cannula 1, and is brought into coupled engagement with the cone of the proximal coupling element 24. The length of the optical system 25 is sufficiently large that its distal extremity projects beyond the oblique face 1a, as is apparent from the illustration of the assembled instrumentation apparatus as shown in FIG. 7.

As required for culdoscopy, the length of the intermediate element 18 may be reduced by grasping the handle elements 20 and 21 and compressing them by the length H as shown in FIG. 7, so that the distal extremity of the optical system 25 then projects in desirable manner from the puncture cannula and may be brought closer to the object.

I claim:

1. Endoscopic instrumentation apparatus for performing laparoscopy and culdoscopy, comprising:
   (a) a puncture cannula presenting a connection for a gas supply having a distal oblique face and a proximal cylindrical casing in which a coupling element constituted by a hollow shaft is installed for displacement against a spring toward the proximal end,
   (b) a hollow mandrel presenting a connection for a gas supply and a related optical system, each of which is respectively and separately connectible to said coupling element of said puncture cannula and when so connected each extending distally beyond said oblique face of said puncture cannula,
   (c) a hollow contractible cylindrical intermediate element comprising contractible parts reducible in length against a spring therein and also connectible to said coupling element of said puncture cannula, said interemediate element being combined with and traversable by an optical system longer than the first when connected therewith and of a length to project distally at least beyond said oblique face of said puncture cannula,
   (d) the contractible length of the intermediate element resulting in the distal end of the longer optical system therein projecting further beyond the oblique face of the cannula by the length of the contraction so the distal end of the second-named optics may be brought that much closer to the object,
   (e) wherein said intermediate element comprises a first hollow cylinder closed off at its distal end by a coupling element complementally engaging in said coupling element of said puncture cannula, a second hollow cylinder closed off at its proximal end and being displaceable in said first hollow cylinder toward the distal end against a spring by means of handles, and wherein a proximal delimitation of said second displaceable, hollow cylinder is provided with a coupling element similar to that of said hollow shaft of said puncture cannula.

* * * * *